United States Patent [19]

Smit et al.

[11] 4,182,329
[45] Jan. 8, 1980

[54] ACNE FACIAL TREATMENT APPLIANCE AND METHOD

[76] Inventors: Helen E. Smit; Julie A. Smit, both of 1045 Hinman Ave., Evanston, Ill. 60202

[21] Appl. No.: 801,850
[22] Filed: May 31, 1977
[51] Int. Cl.² .................................................. A61F 7/00
[52] U.S. Cl. .................................... 128/256; 128/367
[58] Field of Search ............... 128/256, 367, 368, 276

[56] References Cited

U.S. PATENT DOCUMENTS

| 1,965,424 | 7/1934 | Mascolo | 128/256 |
| 1,982,905 | 12/1934 | Davis | 128/256 X |
| 2,267,547 | 12/1941 | Zimmerman | 128/256 |
| 3,511,236 | 5/1970 | Conlin et al. | 128/256 X |
| 3,749,092 | 7/1973 | Williams | 128/256 |
| 3,832,995 | 9/1974 | Welch | 128/256 |

FOREIGN PATENT DOCUMENTS 353955 10/1919 Fed. Rep. of Germany .......... 128/256

Primary Examiner—John D. Yasko
Attorney, Agent, or Firm—Charles A. Laff; J. Warren Whitesel; Howard B. Rockman

[57] ABSTRACT

A personal appliance comprises a vacuum chamber and a steam-generating chamber. Steam is applied to an area of human skin for a period which is long enough to open pores, melt any wax-like substances within the pores, and otherwise cause the skin to be cleaned. Thereafter, a mild suction is applied to the steamed area. In some instances the suction may be applied in a pulsating manner to massage the skin.

17 Claims, 7 Drawing Figures

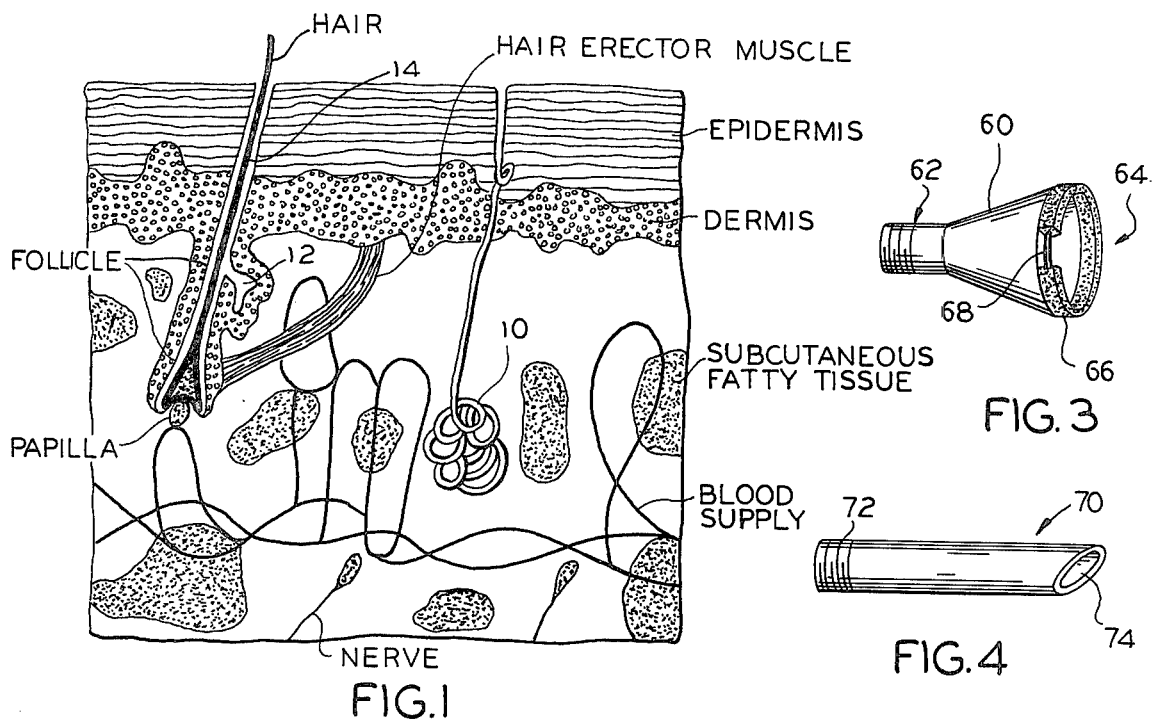

ACNE FACIAL TREATMENT APPLIANCE AND METHOD

This invention relates to an electrical personal appliance combining a sauna bath type of device for softening hardened oil in the pores of the face, or any other human skin areas, and a suction device for cleaning away the softened oil.

Reference is made to a book entitled "Your Skin" by Margaret O. Hyde, McGraw-Hill, publisher, which describes acne as one of the more common human skin ailments. Most persons suffer from some degree of acne during their teenage years, and some continue to face the problems into their adult lives. The usual reason for this teenage affliction is that, during the sexual development of adolescence, the endocrine activity of the glands increases. These endocrine glands affect various parts of the body, including the sebaceous glands of the skin. The oily material, sebum, which these glands produce, tends to collect, harden and clog pores to produce acne.

Actually, the word "acne" encompasses a number of variations and diseases, each with its own characteristics. Basically, acne may take the form of blackheads, whiteheads, pustules, and sometimes deeper boil-like irritations. These blemishes occur most commonly on the face, and sometimes on the neck, shoulders, or chest. Acne is most important for its psychological effects, since it detracts from one's appearance, and may lead to severe and permanent scarring.

Dermatologists usually try to cure acne internally by giving drugs to the patient. With these treatments, it still takes six months or so to clear up even a mild case of acne. While these drugs work on preventing further outbreaks of acne, they do little to clear the existing acne.

Accordingly, an object of the invention is to provide new and improved means for and methods of immediately improving the appearance of a person having acne by cleaning out clogged pores.

Yet another object is to make a patient's skin look better, so that he will be less apt to worry about it, since worrying often produces more oil, which in turn clogs more pores, and exacerbates the acne.

Still another object of the invention is to provide new and improved means for and methods of deeply cleaning human skin.

In keeping with an aspect of the invention, these and other objects are accomplished by providing a steam or sauna type of bath which opens pores, softens hardened oils and tends to cause the softened oils to drain from the pores. Once the pores begin to drain properly, a suction source draws the oils away from the face. The suction may be applied in a pulsating manner to massage the skin.

The appended drawing shows a preferred embodiment of the invention, wherein:

FIG. 1 schematically shows a cross section of human skin and tissue to illustrate how and why acne occurs;

FIG. 2 schematically shows a personal appliance incorporating the invention;

FIG. 3 shows a large area treatment attachment for use with the appliance of FIG. 2;

FIG. 4 shows a small area treatment attachment for use with the appliance of FIG. 2;

FIG. 5 shows a facial mask appliance attachment for use with the appliance of FIG. 2;

FIG. 6 shows a fragmentary cross section of the facial mask of FIG. 5; and

FIG. 7 shows a scalp treatment attachment for use with the appliance of FIG. 2.

As seen in FIG. 1, two sets of glands (the sweat gland 10 and the sebaceous (oil) glands 12) discharge their secretions over the skin. The sebaceous glands' oily secretion, sebum, normally lubricates the skin, keeping it moist and flexible. The sebeceous glands are most numerous on the forehead, chin, and around the nose. When a sebaceous gland becomes overactive, the oil hardens within the duct 14 leading to the surface of the skin. This hardening of the oil causes the duct to expand, which tends to stretch the pore opening, thereby causing it to contract. Then, the pore becomes clogged and plugged up. Therefore, to treat this acne condition, the pore needs to be reopened and the hardened oil needs to be softened. This can be done by steaming the skin area containing the clogged pore. Since heat expands and melts oils and waxes, this steam expands the pore openings and softens the oils. However, steaming alone does not automatically improve acne, because, if the oil remains in the duct 14, it will likely reharden within a short time after the heat is removed. Therefore, the invention preferably contemplates applying a suction to the pore during and directly after a steaming process. The suction removes the liquefied oil, leaving the duct clear, and enabling it to return to normal. However, the sequence and timing of the steaming and vacuuming may vary from person to person.

The inventive personal appliance 30 includes two parts forming a sauna-forming chamber 32 (FIG. 2) and a vacuum-forming chamber 34. The sauna chamber 32 comprises a heating element 36, a removable water and waste collector tray 38, and a steam-collecting hood 40 positioned over tray 38 and leading to hose 42. The vacuum-forming chamber 34 includes a reversible motor 44 and impeller 46. A spring-biased valve 48 normally closes the vacuum-forming chamber 34 from the sauna chamber 32. Normally, the motor runs in one direction to draw a vacuum; however, it may also be run in an opposite direction to blow warm and moist air up the hose 42, in which case, the valve 48 must be opened against the bias of spring 51.

The hood 40 is positioned very near the surface of water in the tray 38, but not so close that it would reduce or interfere with the draft of air drawn into the vacuum chamber. The baffle 49, at the back of the water tray 38, raises high enough above the surface of the water to interfere with any heavy particles in the air stream. Therefore, when the vacuum is drawing air through the hose 42, the light gas atoms will be sucked from hose 42 into the vacuum chamber. However, any heavier particles will have considerable inertia, will continue on a downward path from the hose 42, and will be entrapped by the water.

Any suitable switches 50,52 may be provided, individually and respectively, to control the vacuum 34 and the sauna chamber 32. Each of these switches may be adapted to provide a range of settings extending from "off" through "low" and "medium" to "high." The sauna chamber control switch 52 is connected through a thermostat 54 to heating element 36 to maintain a heating level which is selected by the switch 52.

Depending upon the setting of switch 52, the heating element 36 increases the temperature of the water in tray 38. At a high temperature, the water is vaporized into steam. Positioned above the water 38 is the vaporcollecting hood 40 which receives and collects moisture and heated air that is rising from the water 38. The convection currents generated by the rising stream of hot air pass through the hose 42.

Interposed between the vacuum and sauna chambers is a rotating valve 55 for causing a pulsation of either warm or moist air which is blown over the skin or vacuum which draws the material from the skin. In greater detail, as schematically drawn, a rotor in valve 55 may be in position 57 to block the flow of air or other gas between chambers 32,34. Or, the rotor may be in position 58 to enable such a flow. If the rotor is rotating, the flow of gas is pulsating. The speed of rotation may be varied according to personal needs.

The hose is terminated by any one of many attachments which is held near the face or other body part of the person who is using the vacuum device. The attachments are detachable so that they may be washed. In greater detail, FIG. 3 shows a flaring or a funnel-shaped attachment 60 which is flexible and can fit, at its end 62, on to the end of the hose 42. The outer end 64 of the funnel 60 terminates in a sponge material 66, here shown partially in cross section to illustrate a flexible, yet somewhat stiff, ring 68 embedded therein. The sponge will be slightly porous to the extent that ambient external air may brush over the face and enter the hose 42, when the vacuum is running. This ring 68 may be a steel spring, for example, which adapts itself to the contours of the face while it is held in position. Yet, when the attachment 60 is removed from the face, the spring returns to its normal position.

FIG. 4 shows another attachment 70 which may be made from a fairly rigid material, such as plastic or hard rubber, for example. The end 72 attaches to the hose 42. The end 74 fits a highly localized area which is small enough so that contoured fitting is not required. For example, the end may have an oval contour which is about $1'' \times \frac{1}{2}''$. This appliance is best used around the nose, hairline, or for individual blemishes.

Yet another attachment 80 is seen in FIG. 5, which is in the form of a facial mask. Preferably, the facial mask is moldable to conform to the contours of a face. While the contours may be in any convenient form, mask 80 is here shown as a full-face mask having cutouts for eyes, nose and mouth. Preferably, each of these cutouts is surrounded on the underside of the mask by a suitable material for sealing against the skin. For example, the crosshatched area 82 indicates a location of a sponge rubber gasket which will prevent the steam and suction from reaching the right eye socket of a person wearing the mask.

The facial mask 80 has an unbroken upper surface 84 and a perforated lower surface 86 held in a spaced relationship by a number of posts or supports 88. These two surfaces are sealed together around all edges, as shown at 89 (FIG. 6). The perforations (one of which is numbered 90) are distributed over the inner surface according to the frequency with which acne occurs in that area. In areas where acne is most likely to occur, the perforations are large (as at 90) and in areas where it is less likely to occur, they are small (as at 92).

The facial mask is made from material which is sufficiently rigid so that the two sides will not collapse and come into contact with each other when they are supported in spaced relationship by posts 88. A hose 94 is integrally formed on the mask 80 to enable it to be connected to the hose 42. Thus, there are communication passages extending from the interior of appliance 30, through hoses 42,94, the space between upper and lower surfaces 84,86 and out the perforations 90,92.

To further illustrate that the mask may be adapted to fit any part of the body, FIG. 7 shows an attachment 100 which is adapted to fit over the top of the skull. This mask is constructed similar to the mask of FIG. 5 and has a cross section similar to that shown in FIG. 6. Again, there are upper and lower surfaces 102,104 with supports 106 between them. Hose 108 provides a means for connecting the attachment 100 to the hose 42. Perforations 110 are formed in the lower surface 104 so that moisture and vacuum may reach the skin of a person wearing the skull cap. The bottom 112 of the cap may terminate in an elastic band which seals the skullcap to the head.

The operation of the device should now be clear. An appropriate attachment is placed upon the end of hose 42. The heating element 36 is energized to vaporize the water in tray 38. As the selected attachment is held against the face, steam rises through the hose and to the face. For example, if the funnel 60 is held against a cheek, steam rises to warm and wet the cheek. If desired, the fan motor 44 may be reversed and driven at very low speed to drive the steam vapors toward the face. If so, the valve 48 may be opened manually.

After a suitable period of time, the area of the face encompassed by the attachment will have been bathed in warm moisture-laden air long enough to open the pores and soften embedded wax-like deposits. Then, the vacuum is switched on for a period which is long enough to draw the water, oil or other material from the face. The treatment may be repeated periodically until the pores are cleaned out. If desired, the suction may be made to pulsate to further aid in removing the oil. The pulsation, if used, would also be a form of message for any desired area.

The invention is not limited to treatment of acne, but may be used any time that it is either necessary or desirable to treat skin with heat or moisture or a gentle pulsating suction.

For example, in a book by Carlson Wade, "The Natural Way to Beauty and Health" (New York: Bantam Books, 1968) p. 38–39, there is a case history of a man who was suffering from hair loss and who benefitted from massage and steam treatments. On the first day of the week, this man would apply white iodine to his scalp with a swab of absorbant cotton. On the next day, he would massage the scalp with castor oil. He continued this alternate application of white iodine one day, caster oil and massage the next, etc. On the seventh day, he would soak a towel in hot water and wrap it, steaming, around his head like a turban. He let it remain thirty minutes. He repeated this steaming process five times. Then he shampooed his hair with castile soap. He did this one week every month and claimed that it not only stopped his hair loss but increased hair growth.

Apparently, it is thought that each hair grows from a tiny pocket or follicle in the scalp. In the bottom of this pocket or follicle is a little mound, the papilla, which is the root from which the hair grows. The papilla and the follicle are supplied with blood vessels. Growth of a hair takes place at the junction of the follicle and the papilla. The blood vessels bring cells to the papilla which pushes them up into the follicle where they harden and become a strand of hair. If true, it would appear that, by improving the scalp's circulation, balding people can bring more cells to the papilla which in turn will tend to produce hair.

We do not necessarily endorse this accounting by Carlson Wade. The point is that he, and many others, often prescribe heat or massage treatments calculated to bring blood to a surface of the skin. For many, if not most, of these prescriptions, the inventive device should bring added treatment.

Accordingly, the appended claims are to be construed broadly enough to cover all equivalent structures.

We claim:

1. A personal appliance comprising a housing including means for heating fluids to a steam heat, means for conveying said steam by convection currents directly to an area of skin surface for a predetermined period, valve means for preventing the steam-moistened air from being mixed with and cooled by room air during the conveying of said steam-moistened air to the skin to prevent condensation of said steam into water droplets and to avoid intentionally cooling the steam, and means for thereafter applying a pulsating air suction to the area of skin which is heated by said steam, said housing including a combination of a down-draft hood and a removable tray for catching debris lifted from said area of skin whereby said tray may be lifted out of said appliance to remove said debris and sanitize said tray.

2. The appliance of claim 1 wherein said attachment is a skullcap for stimulating circulation in the scalp of the user, said skullcap having two layers separated by a space communicating with said appliance, and a plurality of perforations on the layer next to the scalp of the person wearing said skullcap, said skullcap being made of a flexible material, and means for supporting said layers so they will not collapse together under suction.

3. The appliance of claim 1 wherein said suction applying means comprises a reversible motor, said motor operating in one direction for driving said moist air toward said skin surface and operating in an opposite direction for sucking waste from said skin area, said reversible motor being situated within a housing having a continuous passageway leading to a hose, wherein said passageway is the same conductor for driving said moist air toward the skin surface and for sucking waste from said skin surface.

4. The appliance of claim 1 wherein said suction applying means comprises a pulsating source of air flow to further aid in dislodging said oil or stimulating said skin area.

5. The appliance of claim 3 and valve means for selectively controlling the direction of air flow toward or away from said skin area.

6. The appliance of claim 1 and valve means for selectively controlling the direction of air flow toward or away from said skin surface.

7. A personal appliance comprising a housing including means for heating fluids to a steam heat means for conveying said steam by convection currents directly to an area of skin surface for a predetermined period, means for preventing the steam-moistened air from being mixed with and cooled by room air during the conveying of said steam-moistened air to the skin to prevent condensation of said steam into water droplets and to avoid intentionally cooling the steam, means for thereafter applying a pulsating air suction to the area of skin, said means for applying a suction to an area of skin comprising a detachable hose and a down-draft hood means for connecting said hose over said source of fluid in a position where heavy particles are entrapped by said fluid while lighter particles may be drawn from said hose, said means for conveying said moist air comprising a plurality of attachments which may be selectively attached to said appliance and then may be detached therefrom and washed, said attachment further comprising means for resting stationarily over and in close contact with said area of skin despite differences in contours of the surface of said skin wherein said steam and suction may be applied directly to said skin area.

8. The appliance of claim 7 wherein one of said attachments comprises a flexible facial mask having two layers separated by a space communicating with said appliance, a plurality of perforations on the layer next to the face of a person wearing said mask, and means for supporting said layers so they will not collapse together under suction.

9. The appliance of claim 8 wherein said attachment is moldable to conform to the contours of an entire human face.

10. The appliance of claim 7 wherein the attachment is a hollow tube having a smooth diagonal end for treating limited areas, as around the nose, hairline, or on individual blemishes.

11. The appliance of claim 7 wherein said attachment is a hollow funnel-shaped tube with a means for molding it to conform to the contours of a specific skin area.

12. The appliance of claim 11 wherein said means for molding said funnel-shaped tube is a shape-retaining spring.

13. The appliance of claim 7 wherein said attachment is a two-layer mask held in a space apart relationship by partition means.

14. The appliance of claim 13 wherein one of said layers is perforated, there being larger ones of said perforations in areas of said mask where treatment is more commonly required and smaller ones of said perforations in areas of said mask where treatment is less commonly required.

15. A process for treating human skin comprising the steps of:
 a. selecting an attachment of a desired size and shape which corresponds to an area of skin to be treated, said selected attachment to be placed in direct contact with the skin area for treatment;
 b. heating a fluid to form a steam sauna bath and exposing a desired area of said skin to air delivered by convection currents from said sauna steam bath to the skin area through said selected attachment, without introduction of cool air into said steam or condensation of said air and steam bathing the skin area for a predetermined period of time to open the skin pores and melt the debris within said skin pores;
 c. vacuuming with pulsation said area of skin after said predetermined period of time to lift said melted debris from within skin pores; and
 d. sucking debris with pulsation from said treated skin area through said selected attachment, and deposited into a removable collection means which may be removed from the machine to wash and clean it.

16. The process of claim 15 and the added steps of:
 c. providing a common appliance having a steam-generating means and a vacuum-forming means, and
 d. switching back and forth between said steam-generating means and said vacuum-forming means.

17. The process of claim 15 and the added steps of controlling the intensity of said steam-generating means and the capacity of said vacuum-forming means.

* * * * *